United States Patent [19]

Cheng et al.

[11] Patent Number: 5,750,571
[45] Date of Patent: May 12, 1998

[54] METHODS AND THERAPEUTIC COMPOSITIONS FOR TREATING CYSTIC FIBROSIS

[75] Inventors: Seng Hing Cheng, Wellesley; Shaona Lee Fang, Sudbury; Henry Hoppe, IV, Acton; Alan Edward Smith, Dover, all of Mass.

[73] Assignee: Genzyme Corporation, Cambridge, Mass.

[21] Appl. No.: 774,127

[22] Filed: Dec. 23, 1996

Related U.S. Application Data

[63] Continuation of Ser. No. 72,708, Jun. 7, 1993, which is a continuation-in-part of Ser. No. 935,603, Aug. 26, 1992, abandoned, which is a continuation-in-part of Ser. No. 613,592, Nov. 15, 1990, abandoned, which is a division of Ser. No. 589,295, Sep. 27, 1990, abandoned, which is a continuation-in-part of Ser. No. 488,307, Mar. 5, 1990, abandoned.

[51] Int. Cl.$^6$ .................... C07K 53/26; C07K 53/125; C07K 53/122; A61K 31/19
[52] U.S. Cl. .................... 514/557; 514/546; 514/549; 514/552; 514/558; 514/560; 514/826; 514/851; 560/205; 560/265; 562/598; 562/606; 562/607
[58] Field of Search .................... 514/546, 549, 514/557, 851, 552, 558, 560, 826; 560/205, 265; 562/598, 606, 607

[56] References Cited

U.S. PATENT DOCUMENTS

| | | | |
|---|---|---|---|
| 4,873,316 | 10/1989 | Meade et al. | 530/412 |
| 5,240,846 | 8/1993 | Collins et al. | 435/240.1 |

FOREIGN PATENT DOCUMENTS

| | | |
|---|---|---|
| 0 446 017 A1 | 9/1991 | European Pat. Off. . |
| WO 91/02796 | 8/1990 | WIPO . |
| WO 91/10734 | 1/1991 | WIPO . |

OTHER PUBLICATIONS

J. Marshall et al. "Stoichiometry of Recombinant Cystic Fibrosis Transmembrane Conductance Regulator in Epithelial Cells and Its Functional Reconstitution into Cells in vitro". *The Journal of Biological Chemistry*, 269, 1994, pp. 2987–2995.

J. Amara et al., "Intracellular protein trafficking defects in human disease", *Trends in Cell Biology*, 2, 1992, pp. 145–149.

C. Li et al., "The cystic fibrosis mutation (ΔF508) does not infuence the chloride channel activity of CFTR", *Nature Genetics*, 3, 1993, pp. 311–316.

W. Dalemans et al., "Altered chloride ion channel kinetics associated with the ΔF508 cystic fibrosis mutation", *Nature*, 354, 1991, pp. 526–528.

M. Drumm et al., "Chloride Conductance Expressed by ΔF508 and Other Mutant CFTRs in xenopus Oocytes", *Science*, 254, 1991, pp. 1797–1799.

C. Machamer et al., "Vesicular Stomatitis Virus G Proteins with Altered Glycosylation Sites Display Temperature-sensitive Intracellular Transport and Are Subject to Aberrant Intermolecular Disulfide Bonding", *The Journal of Biological Chemistry*, 263, 1988, pp. 5955–5960.

Annunziato, A.T. et al., "Treatment with Sodium Butyrate Inhibits the Complete Condensation of Interphase Chromatin", *Chromosoma*, 96:132–138 (1988).

Bates, S.E. et al., "Modulation of P–Glycoprotein Phosphorylation and Drug Transpost by Sodium Butyrate", *Biochemistry*, 31:6366–6372 (1992).

Boggaram, V. et al., "Regulation of Expression of the Gene Encoding the Major Surfactant Protein (SP–A) in Human Fetal Lung in Vitro". *The Journal of Biological Chemistry*, 264:11421–11427 (1989).

Cheng, S.A. et al., "Functional Activation of the Cystic Fibrosis Trafficking Mutant ΔF508–CFTR By Overexpression", *American Journal of Physiology*, 12:L615–L624 (1995).

McKnight, G.S. et al., "Butyrate and Related Inhibitors of Histone Deacetylation Block the Induction of Egg White Genes by Steroid Hormones", *Cell*, 22: 469–477 (1980).

Nichols, K.V. et al., "Regulation of Surfactant Protein A mRNA By Hormones and Butyrate in Cultured Fetal Rat Lung", *American Journal of Physiology*, 259:L448–L495 (1990).

Nichols, K.V. et al., "Inhibition of SP–A mRNA by Butyric Acid Analogs In Fetal Rat Lung Explants" *Pediatric Research*, 27: 49A (1990).

Novogrodsky, A. et al., "Effect of Polar Organic Compounds on Leukemic Cells", *Cancer*, 51:9–14 (1983).

Perrine, S.P. et al., "Butryic Acid Analogues Augment y Globin Gene Expression in Neonatal Erythroid Progenitors", *Biochemical and Biophysical Research Communications*, 148:694–700 (1987).

Cheng, S.H. et al (1993) "Defective Intracellular Processing of CFTR as the Molecular Basis of Cystic Fibrosis" *Cystic–Fibrosis Current Topics:* vol. 1:175–189.

Teem, J.L. et al. (1993) "Identification of Revertants for the Cystic Fibrosis ΔF508 Mutation Using STE6–CFTR Chimeras in yeast" *Cell* 73:335–346.

Welsh, M.J. and Smith, A.E. (1993) "Molecular Mechanisms of CFTR Chloride Channel Dysfunction in Cystic Fibrosis" *Cell* 73:1251–1254.

Perrine, S.P. et al., "Sodium Butyrate Enhances Fetal Globin Gene Expression in Erythroid Progenitors of Patients With HbSS and β Thalassemia", *Blood*, 74:454–459 (1989).

(List continued on next page.)

Primary Examiner—Peter G. O'Sullivan

[57] ABSTRACT

Methods for treating cystic fibrosis are described. The methods involve the administration of a protein enhancing agent, differentiating agent and/or carboxy-compound to a subject afflicted with cystic fibrosis such that mutant cystic fibrosis transmembrane regulator protein present within cystic fibrosis-associated cells becomes functional. Other aspects described include therapeutic compositions and packaged drugs.

24 Claims, 2 Drawing Sheets

OTHER PUBLICATIONS

Peterec, S.M. et al., "Butyrate Modulates Surfactant Protein mRNA in Fetal Rat Lung By Altering mRNA Transcription and Stability", *American Journal of Physiology*, 11:L9–L15 (1994).

Prasad, K.N., "Butyric Acid: A Small Fatty Acid With Diverse Biological Functions", *Life Sciences*, 27:1351–1358 (1980).

Saito, S. et al., "Flow Cytometric and Biochemical Analysis of Dose–Dependent Effects of Sodium Butyrate on Human Endometrical Adenocarcinoma Cells", *Cytometry*, 12:757–764 (1991).

Toscani, A. et al., "Sodium Butyrate in Combination With Insulin or Dexamethasone Can Terminally Differentiate Actively Proliferating Swiss 3T3 Cells Into Adipocytes" *The Journal of Biological Chemistry*, 265: 5722–5730 (1990).

DiTullio, P. et al (1992), "Production of Cystic Fibrosis Transmembrane Conductance Regulator in the Milk of Transgenic Mice" *Bio/Technology* 10:74–77.

Rosenfeld, M.A. et al. (1992) "In Vivo Transfer of the Human Cystic Fibrosis Transmembrane Conductance Regulator Gene to the Airway Epithelium" *Cell* 68:143–155.

Thomas, P.J. et al. (1992) "The Cystic Fibrosis Transmembrane Conductance" *J. Biol. Chem* 267(9):5727–5730.

Welsh, M.J. (1992) "Cystic Fibrosis Transmembrane Conductance Regulator: A Chloride Channel with Novel Regulation" *Neuron* 8:821–829.

Kartner, N. et al. (1992) "Mislocalization of ΔF508 CFTR in Cystic Fibrosis Sweat Gland" *Nature Genetics* 1:321–327.

Denning, G.M. et al. (1992) "Processing of Mutant Cystic Fibrosis Transmembrane Conductance Regulator is Temperature–Sensitive" *Nature* 358:761–764.

Tsui, L–C. (1992) "The Spectrum of Cystic Fibrosis Mutations" *Trends in Genetics* 8(11):392–398.

Denning, G.M. et al. (1992) "Abnormal Localization of Cystic Fibrosis Transmembrane Conductance Regulator in Primary Cultures of Cystic Fibrosis Airway Epithelia" *J. Cell Biol.* 118(3):551–559.

Smith, A.E. (1992) "Emerging Therapies for Cystic fibrosis" Section V–Topics in Biology in *Ann. Rep. Med. Chem.* 27–235–243.

Anderson, M.P. et al. (1991) "Generation of cAMP–Activated Chloride Currents by Expression of CFTR" *Science* 251:679–682.

Kartner, N. et al. (1991) "Expression of the Cystic Fibrosis Gene in Non–Epithelial Invertebrate Cells Produces a Regulated Anion Conductance" *Cell* 64:681–691.

Anderson, M.P. et al. (1991) Demonstration That CFTR IS a Chloride Channel by Alteration of Its Anion Selectivity *Science* 253:202–205.

Rich, D.P. et al. (1991) "Effect of Deleting the R Domain on CFTR–Generated Chloride Channels" *Science* 253:205–207.

Gregory, R.J. et al. (1991) "Maturation and Function of Cystic Fibrosis Transmembrane Conductance Regulator Variants Bearing Mutations in Putative Nucleotide–Binding Domains 1 and 2" *Mol. Cell. Biology* 8(11):3886–3893.

Dork, T. et al. (1991) "Cystic Fibrosis with Three Mutations in the Cystic Fibrosis Transmembrane Conductance Regulator Gene" *Human Genetics* 87:441–446.

Cheng, S.H. et al. (1991) "Phosphorylation of the R Domain by cAMP–Dependent Protein Kinase Regulates the CFTR Chloride Channel" *Cell* 66:1027–1036.

Anderson, M.P. et al. (1991)"Nucleoside Triphosphates are Required to Open the CFTR Chloride Channel" *Cell* 67:775–784.

Hamosh, A. et al. (1991) "Severe Deficiency of Cystic Fibrosis Transmembrane Conductance Regulator Messenger RNA Carrying Nonsense Mutations R553X and W1316X in Respiratory Epithelial Cells of Patients with Cystic Fibrosis" *J. Clin. Invest* 88:1880–1885.

Dalemans, W. et al. (1991) "Altered Chloride Ion Channel Kinetics Associated with the ΔF508 Cystic Fibrosis Mutation" *Nature* 354:526–528.

Dean, M. et al. (1990) "Multiple Mutations in Highly Conserved Residues Are Found in Mildly Affected Cystic Fibrosis Patients" *Cell* 61:863–870.

Cutting, G.R. et al. (1990) "A Cluster of Cystic Fibrosis Mutations in the First Nucleotide–Binding Fold of the Cystic Fibrosis Conductance Regulator Protein" *Nature* 346:366–369.

Drumm, M.L. et al. (1990) "Correction of the Cystic Fibrosis Defect In Vitro By Retrovirus–Mediated Gene Transfer" *Cell* 62:1227–1233.

Gregory, R.J. et al. (1990) "Expression and Characterization of the Cystic Fibrosis Transmembrane Cunductance Regulator" *Nature* 347:382–386.

Rich, D.P. et al. (1990) "Expression of the Cystic Fibrosis Transmembrane Conductance Regulator Corrects Defective Chloride Channel Regulation in Cystic Fibrosis Airway Epithelial Cells" *Nature* 347:358–363.

Kerem, B–S. et al. (1990) "Identification of Mutations in Regions Corresponding to the Two Putative Nucleotide (ATP)–Binding Folds of the Cystic Fibrosis Gene" *Proc. Natl. Acad. Sci.* 87:8447–8451.

Cheng. S.H. et al. (1990) "Defective Intracellular Transport and Processing of CFTR is the Molecular Basis of Most Cystic Fibrosis" *Cell* 63:827–834.

Riordan, J.R. et al. (1989) "Identification of the Cystic Fibrosis Gene: Cloning and Characterization of Complemenatry DNA" *Science* 245:1066–1073.

Rommens, J.H. et al. (1989) "Identification of the Cystic Fibrosis Gene: Chromosome Walking and Jumping" *Science* 245: 1059–1065.

Kerem, B.S. et al. (1989) "Identification of the Cystic Fibrosis Gene: Genetic Analysis" *Science* 245:1073–1080.

Dorin, J.R. et al. (1987) "A Clue to the Basic Defect in Cystic Fibrosis from Cloning the CF Antigen Gene" *Nature* 326:614–617.

Andrews, G.K. et al. (1987) "Butyrate Selectively Activates the Metallothionein Gene in Teratocarcinoma Cells and Induces Hypersensitivity to Metal Induction" *Nucleic Acids Res.* 15(13):5461–5475.

METHODS AND THERAPEUTIC COMPOSITIONS FOR TREATING CYSTIC FIBROSIS

RELATED APPLICATIONS

This application is a continuation application of U.S. patent application Ser. No. 08/072,708, filed Jun. 7, 1993 which is a continuation application of U.S. patent application Ser. No. 07/935,603 filed Aug. 26, 1992, now abandoned, which is a continuation-in-part of U.S. patent application Ser. No. 07/613,592, filed Nov. 15, 1990, now abandoned, which is in turn a divisional application of U.S. patent application Ser. No. 07/589,295, now abandoned, filed Sep. 27, 1990, which is a continuation-in-part application of U.S. patent application Ser. No. 07/488,307, now abandoned, filed Mar. 5, 1990. This application is also related to the subject matter described in U.S. patent application Ser. No. 07/985,478, now abandoned, filed Dec. 2, 1992. The contents of all of the above patent applications are incorporated herein by reference. Definitions of language or terms not provided in the present application are the same as those set forth in the copending applications. Any reagents or materials used in the examples of the present application whose source is not expressly identified also is the same as those described in the copending application, e.g., ΔF508 CFTR gene and CFTR antibodies.

BACKGROUND OF THE INVENTION

Cystic Fibrosis (CF) is the most common fatal genetic disease in humans (Boat et al., 1989). Based on both genetic and molecular analysis, a gene associated with CF was isolated as part of 21 individual cDNA clones and its protein product predicted (Kerem et al., 1989; Riordan et al., 1989; Rommens et al., 1989).

U.S. patent application Ser. No. 488,307 describes the construction of the gene into a continuous strand, expression of the gene as a functional protein and confirmation that mutations of the gene are responsible for CF. (See also Gregory et al., 1990; Rich et al., 1990). The copending patent application also discloses experiments which showed that proteins expressed from wild type but not a mutant version of the cDNA complemented the defect in the cAMP regulated chloride channel shown previously to be characteristic of CF.

The protein product of the CF associated gene is called the cystic fibrosis transmembrane conductance regulator (CFTR) (Riordan et al., 1989). CFTR is a protein of approximately 1480 amino acids made up of two repeated elements, each having six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan et al., 1989; Hyde et al., 1990). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan et al., 1989; Frizzel et al., 1986; Welsh and Liedtke, 1986; Schoumacher et al., 1987; Li et al., 1988; Hwang et al., 1989; Li et al., 1988).

Sequence analysis of the CFTR gene of CF chromosomes has revealed a variety of mutations (Cutting et al., 1990; White et al., 1990; Dean et al., 1990; and Kerem et al., 1989 and 1990). Population studies have indicated that the most common CF mutation, a deletion of the three nucleotides that encode phenylalanine at position 508 of the CFTR amino acid sequence (ΔF508), is associated with approximately 70% of the cases of cystic fibrosis. This mutation results in the failure of an epithelial cell chloride channel to respond to cAMP (Frizzel et al., 1986; Welsh, 1986; Li et al., 1988; Quinton, 1989). In airway cells, this leads to an imbalance in ion and fluid transport. It is widely believed that this causes abnormal mucus secretion, and ultimately results in pulmonary infection and epithelial cell damage.

Studies on the biosynthesis (Cheng et al., Cell 63:827:834 (1990); Gregory et al., Mol. & Cell Biol. 11:3886–3893 (1991)) and localization (Denning et al., J. Cell Biol. 118:551–559 (1992)) of CFTR ΔF508, as well as other CFTR mutants, indicate that many CFTR mutant proteins are not processed correctly and, as a result, are not delivered to the plasma membrane (Gregory et al., Mol. & Cell Biol. 11:3886–3893 (1991)). These conclusions are consistent with earlier functional studies which failed to detect cAMP stimulated Cl- channels in cells expressing CFTR ΔF508 (Rich et al., Nature 347:358–363 (1990); Anderson et al., Science 251:679–682 (1991)).

SUMMARY OF INVENTION

The present invention was based, at least in part, on the discovery that the treatment of cystic fibrosis-associated (CF-associated) cells with butyrate resulted in functional mutant cystic fibrosis transmembrane regulator (CFTR) protein within the CF-associated cells. The butyrate facilitated the delivery of the mutant CFTR to the appropriate location within the CF-associated cell (the plasma membrane) and the mutant CFTR of butyrate-treated cells was capable of generating chloride channels.

Butyrate is a well known differentiating agent. Butyrate also is a protein enhancing agent in that the addition of butyrate to the CF-associated cells resulted in an increased level of intracellular protein within the CF-associated cell, e.g. an increased level of mutant CFTR. The increased level of intracellular protein can lead to the passage of the mutant CFTR by the surveillance of the quality control mechanism present in the endoplasmic reticulum of the CF-associated cell allowing the delivery of the mutant CFTR to the plasma membrane.

The present invention pertains to a method for treating a subject having cystic fibrosis (CF). The method involves the administration of an effective amount of a protein enhancing agent to the subject having CF.

The protein enhancing agent increases the intracellular level of at least one cellular protein in a CF-associated cell such that a mutant CFTR protein generates functional chloride channels in the cells of the subject.

The present invention further pertains to a method for treating a subject's lung epithelia containing a mutant CFTR protein. The method involves contacting a subject's lung epithelia with a protein enhancing agent which increases the level of at least one cellular protein such that a mutant CFTR protein present in the lung epithelia mediates chloride ion transport across the cell membrane.

The present invention even further pertains to a method for treating a subject having CF by administering an effective amount of a differentiating agent or a carboxy-compound to the subject. The mutant CFTR present in CF-associated cells of the subject generates functional chloride channels or mediates chloride ion transport after treatment with the differentiating agent or carboxy-compound.

Other aspects of the present invention include therapeutic compositions and packaged drugs for treating subjects having CF. The therapeutic compositions include a therapeutically effective amount of at least one of the forementioned agents, (protein enhancing agent, differentiating agent or carboxy-compound) and a pharmaceutically acceptable carrier. The packaged drug includes at least one of the forementioned agents and instructions for administrating the agent for treating subjects having CF.

DETAILED DESCRIPTION

Figure 1:
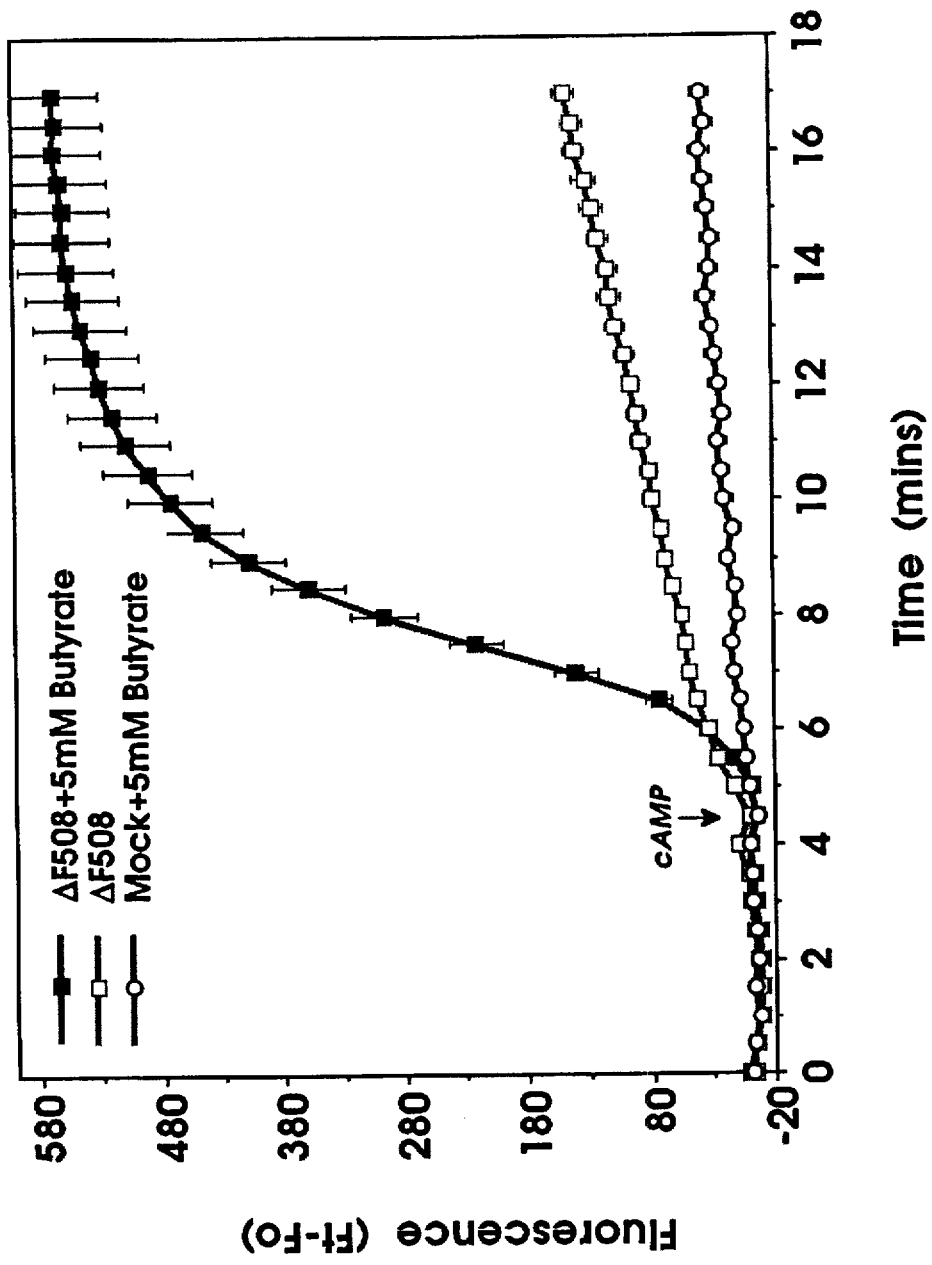
FIG. 1 is a graph depicting the effect of butyrate on recombinant C127-ΔF508 cells.

The present invention pertains to a method for treating a subject having cystic fibrosis (CF). The method involves the administration of a protein enhancing agent to a subject having CF. The protein enhancing agent increases the intracellular level of at least one cellular protein in a CF-associated cell such that a mutant cystic fibrosis transmembrane regulator (CFTR) protein generates functional chloride channels in the CF-associated cell of the subject.

The term subject is intended to include living organisms susceptible to CF, e.g., mammals. Examples of subjects include humans, dogs, cats, horses, cows, goats, rats and mice. The term subject furthers is intended to include transgenic species.

Cystic fibrosis (CF) is a well-known disease state. CF is a disease of infants, children, adolescents, and young adults involving the exocrine glands, especially those secreting mucus. Symptoms associated with CF include pancreatic insufficiency, chronic pulmonary disease, abnormally high sweat electrolyte levels, and, in some cases, cirrhosis of the liver.

The language "protein enhancing agent" is intended to include agents capable of increasing the intracellular level of at least one cellular protein in a CF-associated cell. The protein enhancing agent can increase the expression of the protein by any mechanism as long as the end result is an increased level of at least one cellular protein. For example, the protein enhancing agent can enhance transcription and/or translation. Examples of protein enhancing agents include carboxylates, carboxylic acids, transcription factors (e.g., AP1, PU.1) and proto-oncogenes which enhance transcription. An example of a specific protein enhancing agent is butyrate, particularly sodium butyrate.

The preferred protein enhancing agents of the present invention are those having the following formula:

$$\underset{R-C-OX}{\overset{\overset{\displaystyle O}{\|}}{}} \quad (I)$$

wherein R has one to five carbon atoms and is a moiety selected from the group consisting of alkyl, alkenyl, and alkynyl; and X is hydrogen or a pharmaceutically acceptable salt.

The alkyl, alkenyl, and alkynyl groups (hereinafter "hydrocarbon groups") can be straight or branched chain moieties. The unsaturated groups can have a single site of unsaturation or a plurality of sites of unsaturation. The hydrocarbon groups can contain up to about five carbon atoms, more preferably up to about four carbon atoms, most preferably up to about three carbon atoms. Examples of hydrocarbon groups which can be used in the present invention include methyl, ethyl, ethenyl, ethynyl, propyl, propenyl, propynyl, butyl, butyenyl, butynyl. Examples of branched chain groups include isobutyl and isopropyl.

The language "pharmaceutically acceptable salt" is art-recognized terminology. Typically these salts are capable of being hydrolyzed or solvated under physiological conditions. Examples of such salts include sodium, potassium, and hemisulfate. The term further is intended to include lower hydrocarbon groups capable of being hydrolyzed or solvated under physiological conditions, i.e. groups which esterify the carboxyl group, e.g. methyl, ethyl, and propyl.

The protein enhancing agents of the present invention can be purchased or alternatively can be synthesized using conventional techniques. For example, butyrate, particularly sodium butyrate is commercially available.

The language "effective amount" is intended to include that amount sufficient or necessary to significantly reduce or eliminate a subject's symptoms associated with CF. The amount can be determined based on such factors as the type and severity of symptoms being treated, the weight and/or age of the subject, the previous medical history of the subject, and the selected route for administration of the agent. The determination of appropriate "effective amounts" is within the ordinary skill of the art. This definition applies throughout the present application for all agents including protein enhancing agents, differentiating agents and carboxy-compounds. The term "agent" will be used throughout to refer to these substances collectively.

The term administration is intended to include routes of administration which allow the agent (e.g., protein enhancing agent) to perform its intended function, e.g., increasing the level of at least one cellular protein. Examples of routes of administration which can be used include injection (subcutaneous, intravenous, parenterally, intraperitoneally, etc.), oral, inhalation, transdermal, and rectal. Depending on the route of administration, the agent can be coated with or in a material to protect it from the natural conditions which may detrimentally effect its ability to perform its intended function. The administration of the agent is done at dosages and for periods of time effective to significantly reduce or eliminate the symptoms associated with CF. Dosage regimes may be adjusted for purposes of improving the therapeutic response of the agent. For example, several divided doses may be administered daily or the dose may be proportionally reduced as indicated by the exigencies of the therapeutic situation.

The language "CF-associated cell" is intended to include a cell associated with CF which contains normal and/or mutant CFTR. Examples of such cells include airway epithelial cells such as nasal and lung epithelia.

The language "increase the intracellular level of a cellular protein" is intended to include an increase of the intracellular-level of cellular protein over that level within the cell prior to treatment with the respective agent. The mode for measuring this increase is not an important aspect of this invention as long as it provides a means for comparing the pre-and post-treatment levels. The cellular protein which is increased can be any protein present within the cell. The cellular protein which is increased preferably is CFTR or mutant CFTR.

The terms "CFTR" and "mutant CFTRs" are intended to include normal cystic fibrosis transmembrane regulator and mutant cystic fibrosis transmembrane regulator. The sequence of both the DNA encoding the regulators and the proteins were described previously in the copending applications identified under the Related Applications section. The mutant CFTR proteins include proteins having mutations introduced at residues known to be altered in CF chromosomes (ΔG508, ΔI507, R334W, S5491, G551D) and at residues believed to play an important role in the function of CFTR (e.g., K464N, F508R, N894, 900Q, K1250M). See Example 7 of U.S. patent application Ser. No. 935,603, filed Aug. 26, 1992.

The present invention even further pertains to a method for treating a subject's lung epithelia containing a mutant CFTR protein. The method involves contacting a subject's lung epithelia with the protein enhancing agent which increases the level of at least one cellular protein such that a mutant CFTR protein present in the lung epithelia mediates chloride ion transport across the cell membrane. The subject's lung epithelia can be contacted by administrating the protein enhancing agent to the subject. All other terms are as defined above.

The present invention further pertains to a method for treating a subject having CF by administering an effective amount of a differentiating agent to the subject. The differentiating agent is administered such that a mutant CFTR present in the CF-associated cells of the subject generates functional chloride channels or mediates chloride ion transport.

The language "differentiating agent" is intended to include an agent capable of inducing the differentiation of a cell. Examples of such agents include retinoic acid, other TPA (phorbol esters), DMSO, DMF, interleukins, and protooncogenes capable of inducing differentiation. All other language or terms are as defined above.

The present invention further pertains to a method for treating a subject having CF by administering an effective amount of a carboxy-compound to the subject. The carboxy-compound is administered such that a mutant CFTR present in CF-associated cells of the subject generates functional chloride channels or mediates chloride ion transport.

The language "carboxy-compound" is intended to include compounds which contain a carboxy group

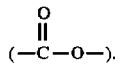

Examples of subgenuses of carboxy-compounds include carboxylic acids and carboxylates. Examples of species of carboxy-compounds include butyric acid and butyrate. The preferred carboxy-compounds are those of formula (I) described above.

The present invention further pertains to therapeutic compositions for treating a subject having CF. The composition contains a therapeutically affective amount of a forementioned agent (protein enhancing agent, differentiating agent, and/or carboxy-compound) and a pharmaceutically acceptable carrier.

The language "therapeutically effective amount" is that amount sufficient or necessary to significantly reduce or eliminate a subject's symptoms associated with CF. The amount can vary depending on such factors as the severity of the symptoms being treated, the size of the subject, or the selected route for administration of the agent.

The language "pharmaceutically acceptable carrier" is intended to include substances capable of being co-administered with the agent and which allow the agent to perform its intended function, e.g. increasing the intracellular level of at least one cellular protein or inducing differentiation. Examples of such carriers include solvents., dispersion media, delay agents and the like. The use of such media and agents for pharmaceutically active substances is well known in the art. Any conventional media and agent compatible with the agent can be used with this invention. The agent of this invention can be administered alone or in a pharmaceutically accepted carrier. The agents further can be administrated as a mixture of agents which also can be in a pharmaceutically acceptable carrier. The agent further can be co-administered with other different art-recognized protein enhancing agents, differentiating agents, and/or adjuvants.

The present invention further pertains to a packaged drug for treating a subject having CF. The packaged drug includes a container holding an agent described above and instructions for administering the agent for treating a subject having CF. Examples of containers include vials, syringes, etc. The instructions would contain dosage information for administering the agent as described above.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLE 1

The Effect of Sodium Butyrate on Recombinant C127 Cells Expressing ΔF508 Cystic Fibrosis Transmembrane Regulator Protein Derivation of ΔF508-C127 Cells A bovine-papilloma virus based eukaryotic expression vector (pBPV-CFTR-ΔF508) containing the gene for ΔF508 CFTR and neomycin resistance were transfected into C127 cells. The C127 cells are murine mammary cells which were obtained from ATCC (#CRL 1616). The expression of the mutant ΔF508 protein and neomycin was driven using a metallothionein promoter. Following transfection, clonal cells resistant to G418 were isolated and cells expressing the mutant ΔF508 protein were subsequently identified using antibodies specific for CFTR (mAb-13-1). The cells expressing the mutant ΔF508 CFTR protein were maintained in Dulbecco's modified eagle's media supplemented with glutamine and fetal calf serum.

Treatment of the ΔF508-C127 Cells with Butyrate and Analysis of Cells for Chloride Channel Activity Recombinant C127 cells expressing ΔF508 CFTR were seeded onto glass coverslips. The cells were treated with butyrate (sold as sodium butyrate by Sigma Chemical, St. Louis, MO.) (5 mM to 50 mM concentrating in cell growth medium) twenty-four hours after seeding for eighteen to twenty-four hours. After treatment with the butyrate, the cells were analyzed for the presence of cAMP-activatable chloride channels using the 6-methoxy-N-[3-sulfopropyl]-quinolinium (SPQ) assay. The cAMP-dependent chloride activity of the mutant CFTR was assessed using the halide-sensitive fluorophore SPQ. The cells were loaded with SPQ by including 10 mM SPQ in the growth media for nine to twelve hours. The SPQ fluorescence was initially quenched by incubating the cells in a sodium iodide buffer solution (135 mM NaI, 2.4 mM $K_2HPO_4$; 0.6 mM $KH_2PO_4$; 1.0 mM $MgSO_4$; 1.0 mM $CaSO_4$; 10.0 mM HEPES pH 7.4). After measuring the fluorescence for two minutes using a Nikon inverted microscope, a Universal Imaging System and a Hamatsu camera, the sodium iodide buffer solution was replaced by a sodium nitrate buffer solution (same as the NaI solution except $NaNO_3$ was substituted for NaI). The fluorescence was measured for an additional 17.5 minutes. SPQ fluorescence is quenched by iodide but not by nitrate. The intracellular cAMP levels were increased by adding forskolin and 3-isobutyl-1-methyl-xanthene (IBMX) five minutes after the anion substitution. In this assay (hereinafter the SPQ assay) an increase in halide permeability results in SPQ fluorescence.

As shown in FIG. 1, the pretreatment of recombinant ΔF508-C127 cells with butyrate resulted in the generation of cAMP-dependent chloride channel activity. Approximately 80–90% of the cells exhibited a rapid increase in fluorescence following stimulation with forskalin and IBMX (which raises intracellular levels of cAMP). These cells therefore contained functional cAMP-dependent chloride channels. This activity was absent from ΔF508-C127 cells which had not been pretreated with butyrate and mocktransfected cells. Mock transfected cells are C127 cells which had been transfected with the bovine-papilloma virus expression vector but not the ΔF508 mutant CFTR gene. These cells express the neomycin resistance gene product but not the mutant CFTR.

EXAMPLE 2

The Effect of Sodium Butyrate on Airway Epithelial Cells Derived from a Subject Having Cystic Fibrosis Derivation of Airway Epithelial Cells The human ΔF508 airway epithelial cells (DF) were derived from tissues of a CF patient homozygous for the ΔF508 mutation (gift from Dr. D. Jefferson, Tufts University, Mass.). The nasal epithelial cells were immortalized by SV40 Large-T antigen transduced using retroviruses. The DF cells were maintained in Dulbecco's modified eagle's media supplemented with adenine, insulin, transferrin, triodothyronine, epidermal growth factor and fetal calf serum.

Figure 2:
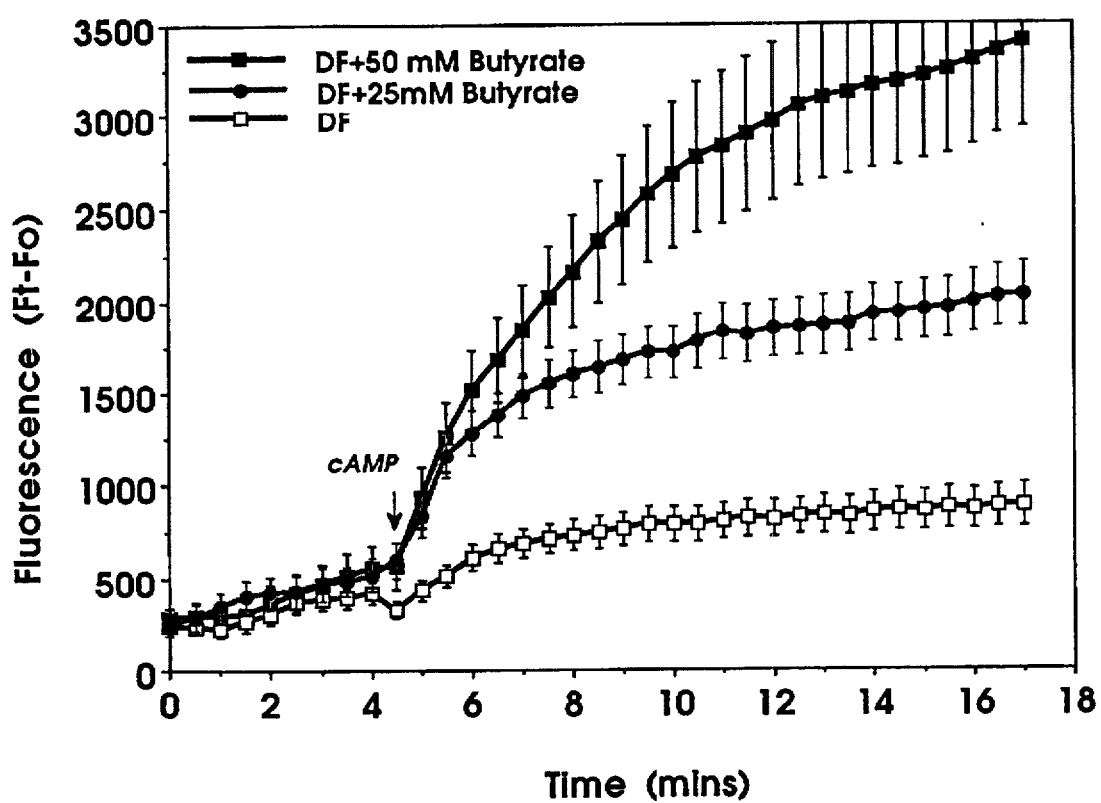
FIG. 2 is a graph depicting the effect of butyrate on ΔF508 airway epithelial cells.

Treatment of the Airway Epithelial Cells with Butyrate and Analysis of the Cells for Chloride Channel Activity The DF cells were treated with butyrate and analyzed for chloride channel activity as described in Example 1 above. As shown in FIG. 2, the pretreatment of DF cells with butyrate resulted in the generation of cAMP-dependent chloride channel activity. Approximately 10–20% of the cells displayed a measurable increase in fluorescence following induction by forskolin and IBMX. The smaller percentage of affected cells in this example probably reflected the lower level of expression of the ΔF508 CFTR protein in these cells (10–100 fold lower). The lower amount of ΔF508 CFTR protein in these cells may have precluded detection because of the limits of the sensitivity using this system.

REFERENCES

Boat, T., Welsh, M. J., and Beaudet, A. (1989). Cystic fibrosis. In: *The Metabolic Basis of Inherited Disease*, C. Scriver, A. Beaudet, W. Sly, and D. Valle, eds. (McGraw Hill, N.Y), pp. 2649–2860.

Cheng, S. H., Harvey, R., Espino, P. C., Semba, K., Yamamoto, T., Toyoshima, K., and Smith, A. E. (1988). Peptide antibodies to the human c-fyn gene product demonstrate pp50$^{c\text{-}fyn}$ is capable of complex formation with the middle-T antigen of polyomavirus. *EMBO J.* 5:325–334.

Cheng, S. H., Rich, D. P., Marshall, J., Gregory, R. J., Welsh, M. J., and Smith, A.E. (1991). Phosphorylation of the R Domain by cAMP-Dependent Protein Kinase Regulates the CFTR Chloride Channel. *Cell* 66:1027–1036.

Cleveland, D. W., Fischer, S. G., Kirschner, M. W., and Laemmli, U. K. (1977). Peptide mapping by limited proteolysis in sodium dodecyl sulfate and analysis by gel electrophoresis. *J. Biol. Chem.* 252:1102–1106.

Cohen, S. N., Chang, A. C. Y., Boyer, H. W., and Helling, R. B. (1973). Construction of biologically functional bacterial plasmids in vitro. *Proc. Natl. Acad. Sci. USA* 70:3240–3244.

Cutting, G. R., Kasch, L. M., Rosenstein, B. J., Zielenski, J., Tsui, L.-C., Antonarakis, S. E., and Kazanian, H. H. (1990a). A cluster of cystic fibrosis mutations in the first nucleatide binding fold of the cystic fibrosis conductance regulator protein. *Nature* 346, 366–369.

Cutting, G. R., Kasch, L. M., Rosenstein, B. J., Tsui, L.-C., Kazanian, H. H., and Antonarakis, S. E. (1990b). Two cystic fibrosis patients with mild pulmonary disease and nonsense mutations in each CFTR gene. *Am. J. Hum. Genet.* 47:213.

Dean, M., White, M. B., Amos, J., Gerrard, B., Stewart, C., OSKhaw, K.-T., and Leppart, M. (1990). Multiple mutations in highly conserved residues are found in mildly affected cystic fibrosis patients. *Cell* 61:863–870.

Dennig, G. M., Anderson, M. P., Amara, J. F., Marshall, J., Smith, A. E., and Welsh, M. J. (1992). Processing of mutant cystic fibrosis transmembrane conductunce regulator is temperature-sensitive. *Nature* 258:761–764.

Drumm, M. L., Pope, H. A., Cliff, W. H., Rommens, J. M., Marvin, S. A., Tsui, L.-C., Collins, F.S., Frizzel, R. A., and Wilson, J. M. (1990). Correction of the cystic fibrosis defect in vitro by retrovirus-mediated gene transfer. *Cell* 62:1227–1233.

Frizzell, R. A., Rechkemmer, G., and Shoemaker, R. L. (1986). Altered regulation of airway epithelial cell chloride channels in cystic fibrosis. *Science* 233:558–560.

Gregory, R. J., Cheng, S. H., Rich, D. P., Marshall, J., Paul, S., Hehir, K., Osteggaard, L., Klinger, K. W., Welsh, M. J., and Smith, A. E. (1990). Expression and characterization of the cystic fibrosis transmembrane conductance regulator. *Nature* 347:382–386.

Harlow, E., Crawford, L. V., Pim, D. C., and Williamson, N. M. (1981). Monoclonal antibodies specific for simian virus 40 tumor antigens. *J. Virol.* 39:861–869.

Harper, P. S. (1989). The muscular dystrophies. In: *The Metabolic Basis of Inherited Disease*. C. Scriver, A. Beaudet, W. Sly, and D. Valle, eds. (McGraw Hill, N.Y.), pp. 2869–2904.

Hurtley, S. M., and Helenius, A. (1989). Protein allgomerization in the endoplasmic reticulum. *Ann. Rev. Cell Biol.* 5:377–307

Hyde, S. C., Emsley, P., Hartshorn, M. J., Mimmack, M. M., Gileadi, U., Pearce, S. R., Gallagher, M. P., Gill, D. R., Hubbard, R. E. and Higgins, C. F. (1990). Structural model of the ATP-binding proteins associated with cystic fibrosis, multidrug resistance and bacterial transport. *Nature* 346:362–365.

Hwang, T.-C., Lo., L., Zellin, P. L., Gruenert, D. C., Huganir, R., Guggino, W. B. (1989). Cechannels on CF: Lack of Activation by Protein Kinase C and cAMP-Dependent Protein Kinase. *Science* 244:1351–3.

Kalderon, D., Richardson, W. D., Markham, A. F., and Smith, A. E. (1985). Sequence requirements for nuclear location of simian virus 40 large-T antigen. *Nature* 311:33–38.

Kerem, B.-S., Rommens, J. M., Buchanan, J. A., Markiewicz, D., Cox, T. K., Chakravarti, A., Buchwald, M., and Tsui, L.-C. (1989). Identification of the cystic fibrosis gene: genetic analysis. *Science* 245:1073–1080.

Kerem, B.-S., Zielenski, J., Markiewicz, D., Bozon, D., Gazit, E., Yahaf, J., Kennedy, D., Riordan, J. R., Collins, F.

S., Rommens, J. R., and Tsui, L.-C. (1990). Identification of mutations in regions corresponding to the two putative nucleotide (ATP)-binding folds of the cystic fibrosis gene. *Proc. Natl. Acad. Sci. USA* 87:8447–8451.

Klausner, R. D., and Sitia, R. (1990). Protein degradation in the endoplasmic reticulum. *Cell* 62:611–614.

Kunkel, T. M. (1985). Rapid and efficient site-specific mutagenesis with phenatypic selection. *Proc. Natl. Acad. Sci. USA* 82:488–492.

Laemmli, U. K. (1970). Cleavage of structural proteins during assembly of the head of bacteria T4. *Nature* 227:680–685.

Lehrman, M. A., Schneider, W. J., Brown, M. S., Davis, C. G., Elhammer, A., Russell, D. W., and Goldstein, J. L. (1986). The Lebanese allele at the low density lipoprotein receptor locus. Nonsense mutation produces truncated receptor that is retained in endoplasmic reticulum. *J. Biol. Chem.* 262:401–410.

Li, M., McCann, J. D., Liedtke, C. M., Nairn, A. C., Greengard, P., and Welsh, M. J. (1988). Cyclic AMP-dependent protein kinase opens chloride channels in normal but not cystic fibrosis airway epithelium. *Nature* 331:358–360.

Lodish, H. F. (1988). Transport of secretary and membrane glycoproteins from the rough endoplasmic reticulum to the golgi. *J. Biol. Chem.* 263:2107–2110.

Pelham, H. R. B. (1989). Control of protein exit from the endoplasmic reticulum. *Ann. Rev. Cell Biol.* 5:1–23.

Quinton, P. M. (1989). Defective epithelial ion transport in cystic fibrosis. *Clin. Chem.* 35:726–730.

Rich, D. P., Anderson, M. P., Gregory, R. J., Cheng, S. H., Paul, S., Jefferson, D. M., McCann, J. D., Klinger, K. W., Smith, A. E., and Welsh, M. J. (1990). Expression of the cystic fibrosis transmembrane conductance regulator corrects defective chloride channel regulation in cystic fibrosis airway epithelial cells. *Nature* 347:358–363.

Riordan, J., Rommens, J. M., Kerem, B.-S., Alon, N., Rozmahel, R., Grzelczack, Z., Zielenski, J., Lok, S., Plavsic, N., Chou, J. L., Drumm, M. L., Iannuzzi, M. C., Collins, F. S., and Tsui, L.-C. (1989). Identification of the cystic fibrosis gene cloning and characterization of the complementary DNA. *Science* 245:1066–1073.

Rommens, J. H., Iannuzzi, M. C., Kerem, B.-S., Drumm, M. L., Melmer, G., Dean, M., Rozmahel, R., Cole, J. L., Kennedy, D., Hidaka, N., Zsiga, M., Buchwald, M., Riordan, J. R., Tsui, L.-C., and Collins, S.F. (1989). Identification of the cystic fibrosis gene: chromosome walking and jumping. *Science* 245:1059–1065.

Rose, J. K., and Dorns, R. W. (1988). Regulation of protein export from the endoplasmic reticulum. *Ann. Rev. Cell Biol.* 4:257–288.

Sambrook, J., Fritsch, E. F., and Maniatis, T. (1989). Molecular Cloning: A Laboratory Manual (Cold Spring Harbor, N.Y.: Cold Spring Harbor Laboratory).

Weatherall, D. S., Clegg, J. B., and Wood, W. G. (1989). The hemaglobinopathies. In: The Metabolic Basis of Inherited Disease, C.Scriver, A. Beaudet, W. Sly, and D. Valle, eds. (McGraw Hill, N.Y.), pp. 2281–2340.

Welsh, M. J. (1986). An apical-membrane chloride channel in human tracheal epithelium. *Science* 232:1648–1650.

Welsh, M. J. and Liedtke, C. M. (1986). Chloride and Potassium Channels in Cystic Fibrosis Airway Epithelia *Nature* 322:467.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method for treating defective chloride ion transport in a subject having cystic fibrosis said method comprising:
   administering to said subject an agent selected from the group consisting of differentiating agents, protein enhancing agents and carboxy-compounds in an amount effective to transport mutant cystic fibrosis transmembrane regulator (CFTR) protein to the plasma membrane of a cystic fibrosis (CF)-associated cell of said subject; and
   mediating mutant CFTR chloride ion transport in the CF-associated cell of said subject.

2. The method of claim 1 wherein said mutant CFTR generates chloride channels in the CF-associated cell of said subject.

3. The method of claim 1 wherein said agent is a compound having the following formula:

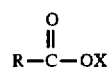

wherein R is a carboxyl moiety having from about one to about five carbon atoms selected from the group consisting of alkyls, alkenyls and alkynyls; and X is a hydrogen atom or a pharmaceutically acceptable salt.

4. The method of claim 1 wherein the CF-associated cell is an epithelial cell.

5. The method of claim 4 wherein the epithelial cell is an airway epithelial cell.

6. A packaged drug comprising:
   a container holding an agent for treating defective chloride ion transport in a subject having cystic fibrosis, said agent selected from the group consisting of differentiating agents, protein enhancing agents and carboxy-compounds; and
   instructions for administering to said subject the agent for treating defective chloride ion transport in said subject.

7. The packaged drug of claim 6 wherein said agent is a compound having the following formula:

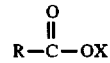

wherein R is a carboxyl moiety having from about one to about five carbon atoms selected from the group consisting of alkyls, alkenyls and alkynyls; and X is a hydrogen atom or a pharmaceutically acceptable salt.

8. A method for generating chloride channels in a cystic fibrosis (CF)-associated cell, the method comprising:
   contacting said cell with an amount of an agent selected from the group consisting of differentiating agents, protein enhancing agents and carboxy-compounds, said agent effective to mobilize mutant cystic fibrosis transmembrane regulator protein in said cell such that said mutant cystic fibrosis transmembrane regulator protein is transported to the plasma membrane of said cell; and
   generating chloride channels in said CF-associated cell.

9. The method of claim 8 wherein the CF-associated cell is an epithelial cell.

10. The method of claim 9 wherein the epithelial cell is an airway epithelial cell.

11. The method of claim 8 wherein said agent is a compound having the following formula:

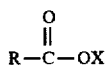

wherein R is a carboxyl moiety having from about one to about five carbon atoms selected from the group consisting of alkyls, alkenyls and alkynyls; and X is a hydrogen atom or a pharmaceutically acceptable salt.

12. The method of claim 11 wherein the pharmaceutically acceptable salt is selected from the group consisting of sodium, potassium and hemisulfate.

13. A method for generating chloride channels in a cystic fibrosis (CF)-associated cell, the method comprising administering to said cell an agent selected from the group consisting of differentiating agents, protein enhancing agents and carboxy-compounds in an amount effective to mobilize mutant cystic fibrosis transmembrane regulator protein in said cell such that said mutant cystic fibrosis transmembrane regulator protein is transported to the plasma membrane of said cell; and generating chloride channels in said CF-associated cell.

14. The method of claim 13 wherein the CF-associated cell is an epithelial cell.

15. The method of claim 14 wherein the epithelial cell is an airway epithelial cell.

16. A method according to claim 3, wherein said pharmaceutically acceptable salt is selected from the group consisting of sodium, potassium, hemisulfate and lower hydrocarbon groups capable of being hydrolyzed or solvated under physiological conditions.

17. A packaged drug according to claim 7, wherein said pharmaceutically acceptable salt is selected from the group consisting of sodium, potassium, hemisulfate and lower hydrocarbon groups capable of being hydrolyzed or solvated under physiological conditions.

18. A method according to claim 11, wherein said pharmaceutically acceptable salt is selected from the group consisting of sodium, potassium, hemisulfate and lower hydrocarbon groups capable of being hydrolyzed or solvated under physiological conditions.

19. The method of claim 18 wherein the lower hydrocarbon group esterifies the carboxyl moiety and is selected from the group consisting of methyl, ethyl and propyl.

20. A method according to claim 16 wherein the lower hydrocarbon group esterifies the carboxyl moiety and is selected from the group consisting of methyl, ethyl and propyl.

21. A packaged drug according to claim 17 wherein the lower hydrocarbon group esterifies the carboxyl moiety and is selected from the group consisting of methyl, ethyl and propyl.

22. A method according to claim 3, wherein said agent is in a pharmaceutically acceptable carrier.

23. A packaged drug according to claim 7, wherein said agent is in a pharmaceutically acceptable carrier.

24. A method according to claim 11, wherein said agent is in a pharmaceutically acceptable carrier.

* * * * *